United States Patent [19]

Faries, Jr. et al.

[11] Patent Number: 5,402,644
[45] Date of Patent: Apr. 4, 1995

[54] METHOD FOR MAINTAINING STERILE SLUSH

[75] Inventors: Durward I. Faries, Jr., McLean; Mark Licata, Richmond, both of Va.

[73] Assignee: O.R. Solutions, Inc., Reston, Va.

[21] Appl. No.: 213,807

[22] Filed: Mar. 16, 1994

[51] Int. Cl.6 .......................................... F25B 21/02
[52] U.S. Cl. ......................................... 62/3.6; 62/66; 62/135
[58] Field of Search .................... 62/66, 135, 136, 137, 62/138, 75, 332, 78, 3.2, 3.6; 604/113; 607/113

[56] References Cited

U.S. PATENT DOCUMENTS

| | | | |
|---|---|---|---|
| 4,393,659 | 7/1983 | Keyes et al. | 62/66 |
| 4,474,016 | 10/1984 | Winchell | 62/78 |
| 4,934,152 | 6/1990 | Templeton | 62/66 |
| 5,163,299 | 11/1992 | Faries, Jr. et al. | 62/66 |
| 5,331,820 | 7/1994 | Faries et al. | 62/68 |
| 5,333,326 | 8/1994 | Faries et al. | 604/113 |

Primary Examiner—John M. Sollecito

[57] ABSTRACT

Sterile surgical slush is maintained at substantially its freezing temperature to prevent both melting and formation of solid ice pieces. The slush is initially formed in a refrigeration mode wherein a basin containing sterile fluid medium is cooled to well below the freezing temperature of the medium to thereby rapidly lower the medium temperature. Upon formation of the slush the system is placed in a maintain mode wherein the container temperature is kept at the freezing temperature of the medium. In the preferred embodiment the maintain mode is effected by electrically energizing one or more thermoelectric modules and deenergizing a refrigeration system in which the refrigerant fluid is passed through an evaporator disposed in thermal energy transfer relation to the basin. In alternative embodiments the refrigeration system itself is controlled to keep the container temperature at the freezing point during the maintain mode.

13 Claims, 4 Drawing Sheets

METHOD FOR MAINTAINING STERILE SLUSH

BACKGROUND OF THE INVENTION

1. Technical Field

The present invention pertains to methods and apparatus for producing sterile slush for use in surgical procedures. The invention is an improvement of the methods and apparatus disclosed in U.S. Pat. Nos. 4,393,659 (Keyes et al), 4,934,152 (Templeton) and 5,163,299 (Faries, Jr. et al). The entire disclosures of those patents are expressly incorporated herein.

The invention is also an improvement of the methods and apparatus disclosed in the following co-pending and commonly owned patent applications: U.S. patent application Ser. No. 08/125,279, filed Sept. 23, 1993 by Durward I. Faries, Jr., Bruce Heymann and Mark Licata, now U.S. Pat. No. 5,331,820, and entitled "Method and Apparatus for Producing Surgical Slush and Heated Sterile Liquid", and U.S. patent application Ser. No. 08/033,639, filed Mar. 16, 1993 by Durward I. Faries, Jr. and Bruce Heymann, now U.S. Pat. No. 5,333,326, and entitled "Method and Apparatus for Producing Sterile Slush". The entire disclosures of those patent applications are also expressly incorporated herein.

2. Discussion of the Prior Art:

The above-referenced Keyes et al patent discloses a surgical slush producing system having a cabinet with a heat transfer basin at its top surface. A refrigeration mechanism in the cabinet takes the form of a closed refrigeration loop including: an evaporator in heat exchange relation to the outside surface of the heat transfer basin; a compressor; a condenser, and a refrigeration expansion control. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. The refrigeration unit is arranged to refrigerate the heat transfer basin to a temperature below the freezing temperature of the liquid used to form the slush. That temperature is described in the patent as being on the order of 25° F. to 28° F. A scraping tool is utilized to remove congealed sterile material from the product basin side to thereby form a slush of desired consistency within the product basin.

The Keyes et al patent describes the sterile fluid as being suitable for subcutaneous administration and preferably approximately isotonic, an example of which is a normal (0.85-0.9%) sodium chloride solution. The refrigerant expansion control is described as possibly being of the type that operates in response to the temperature of the heat exchange basin to control the flow of refrigerant to the evaporator in a manner to maintain the temperature at the heat exchange basin at a preselected value below the freezing temperature of the sterile liquid.

As noted in the above-referenced Templeton patent, the Keyes et al system has a number of disadvantages. In particular, the separate product basin must be removed and re-sterilized after each use. Additionally, the glycol or other thermal transfer medium is highly flammable or toxic and, in any event, complicates the procedure. The Templeton patent discloses a solution to these problems by means of an apparatus wherein the product basin is eliminated in favor of a sterile drape impervious to the sterile surgical liquid, the drape being made to conform to the basin and directly receive the sterile liquid. Congealed liquid is scrapped or chipped from the sides of the conformed drape receptacle to form the desired slush.

The system disclosed in the Templeton patent has two operating modes. In one mode the basin is cooled to a temperature below the freezing point of the sterile liquid. In the other mode the contents of the basin are heated to a temperature slightly elevated with respect to normal human body temperature, typically on the order of 105° F.

A problem with both the Keyes et al and Templeton systems is that, with respect to providing surgical slush, they are either on or off. When the system is on, the basin is cooled to below the freezing temperature of the sterile medium to form the slush. If the systems are kept in the on mode too long, the medium freezes further to form solid chunks of ice. When the systems are turned off, the sterile medium melts. What is needed for surgical use, however, is a semi-frozen slush phase of the medium.

It is also noted that, in the cool or on mode of the Keyes et al system, the heat exchange basin is cooled to 25° F. to 28° F., i.e., only a few degrees below the freezing point of the sterile medium. This has the disadvantage of taking an inconveniently long time to cool the basin and the sterile medium to the desired temperature. The Templeton patent is silent as to the temperature to which the basin is cooled.

OBJECTS AND SUMMARY OF THE INVENTION

It is an object of the present invention to provide a method and apparatus for providing surgical slush from a sterile fluid medium wherein the medium, in liquid form, is rapidly cooled and then may be maintained substantially at its freezing temperature to assure a continued semi-frozen or slush-like consistency throughout a surgical procedure.

In accordance with the present invention, a surgical slush machine of the type described above has a refrigeration mode wherein the heat exchange basin is cooled to a temperature in the range of −10° F. to −70° F. (nominally about −40° F.) to quickly bring the sterile liquid temperature down to its freezing temperature. In a second operating mode, called the maintain mode, the basin temperature is maintained near the freezing temperature of the sterile medium, typically in the range of 20° F. to 40° F. For a 0.9% sodium chloride solution, the freezing temperature is 30.9° F. In a preferred embodiment of the invention, in the maintain mode of operation, the basin temperature is kept at 30.9° F. plus or minus 2%, whereby the slush neither freezes nor melts.

The maintain mode can be actuated manually, automatically by timer control, or automatically by thermostat control in response to the sensed temperature of the basin and/or the sterile medium.

The above and still further objects, feature and advantages of the present invention will become apparent upon consideration of the following detailed description of specific embodiments, particularly when taken in conjunction with the accompanying drawings wherein like reference numerals in the various figures are utilized to designate like components.

DESCRIPTION OF THE PREFERRED EMBODIMENTS

Figure 1:
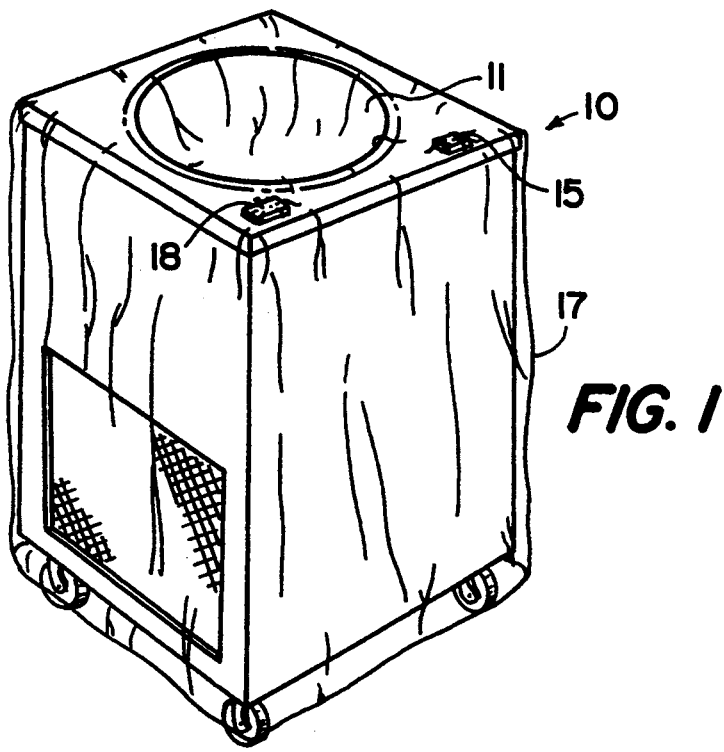
FIG. 1 is a view in perspective of a surgical slush machine of the type employed in the present invention.
Figure 2:
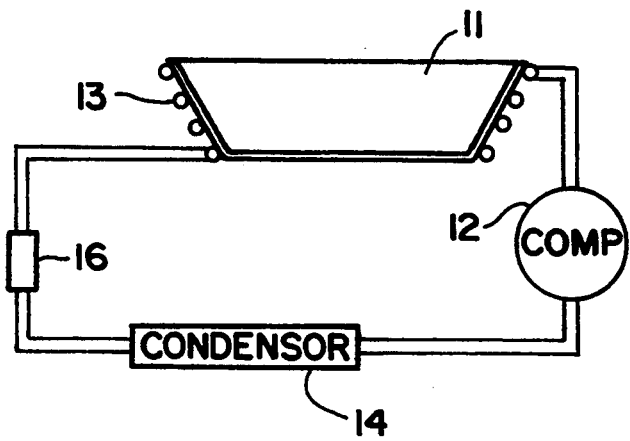
FIG. 2 is a refrigerant flow schematic diagram of a refrigeration system utilized in the machine of FIG. 1.

Referring to FIGS. 1 and 2 of the accompanying drawings, a surgical slush generating system of the type generally described in the above-referenced Templeton patent includes a cabinet 10 with a top surface having a basin 11 mounted thereon in an appropriately sized recess. Basin 11 is made of thermally conductive material, typically stainless steel, and includes a generally flat bottom wall and a frusto-conical side wall. A conventional refrigeration unit is disposed within cabinet 10 and typically includes a compressor 12, a condenser 14 and an expansion control unit 16 connected by appropriate fluid conduits in a closed refrigeration loop with an evaporator 13. The evaporator is in the form of a coil wound about the exterior surface of basin 11 in thermal transfer relation therewith. When the refrigeration unit is activated by means of a power switch 15 located on the top surface of cabinet 10, evaporator 13 cools the side wall of basin 11 to a temperature well below the freezing temperature of the sterile liquid medium used in forming the sterile slush. This temperature is preferably on the order of $-10°$ F. to $-70°$ F., and typically $-40°$ F.

A sterile drape 17, preferably transparent, is disposed over the top and sides of cabinet 10 and made to conform to the side wall and bottom of basin 10. The portion of drape 17 disposed in the basin serves as a sterile receptacle for sterile medium in liquid form placed therein to be frozen into the desired sterile slush. Typical sterile liquid used for this purpose is a 0.80% to 0.95% sodium chloride solution (i.e., saline). Drape 17 is made from a material that is impervious to the sterile liquid and sufficiently soft and flexible to conform to the basin wall. The drape may alternatively have a preformed section contoured to match the contour of the basin. The thickness of the drape is preferably minimized to render thermal transfer therethrough most efficient, yet the thickness is sufficient to resist tearing and puncturing during normal use. Typically, by way of example only, the drape may be made of materials commonly employed in hospitals for surgical drapes and has a thickness in the range of 3.0 to 10.0 mils. Drape 17 may also be made of polyurethane film as disclosed for the drape in the aforementioned Templeton patent. The drape is designed to be disposable after a single use and is provided pre-sterilized and pre-packaged in a manner to preserve its sterile state during storage.

Figure 3:
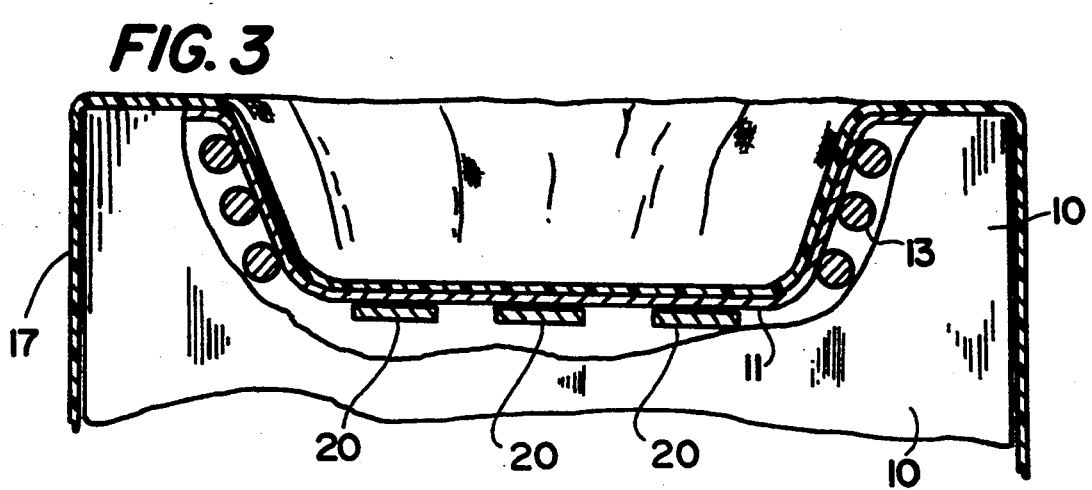
FIG. 3 is a view in elevation and partial section of a portion of the machine of FIG. 1, illustrating in detail one embodiment of the present invention.

According to the present invention the surgical slush machine is provided with an additional mode of operation wherein the slush formed in the manner described above is maintained at the freezing point of the sterile medium to prevent formation of large solid ice chunks while also preventing return of the medium to its liquid phase. Referring to FIG. 3 of the accompanying drawings, in one embodiment of the invention, one or more thermoelectric modules 20 are secured in thermal transfer relative to basin 11. Modules 20 are shown secured to the outside surface of the bottom of basin 11, but the modules could also be secured to the basin side wall. Thermoelectric modules 20 are well known commercially available units, typically formed from a plurality of thermocouple elements fabricated from thermoelectric material such as quaternary alloy of bismuth, tellurium, selenium and antimony with small amounts of suitable dopants. Utilization and mounting arrangements for such modules are well known and are described, for example, in U.S. Pat. Nos. 3,821,881 (Harkias), 4,627,242 (Beitner) and 4,996,847 (Zickler). When appropriately mounted, thermoelectrical modules respond to electrical current passing therethrough to draw heat from (i.e., to cool) the surface on which they are mounted.

Figure 4:
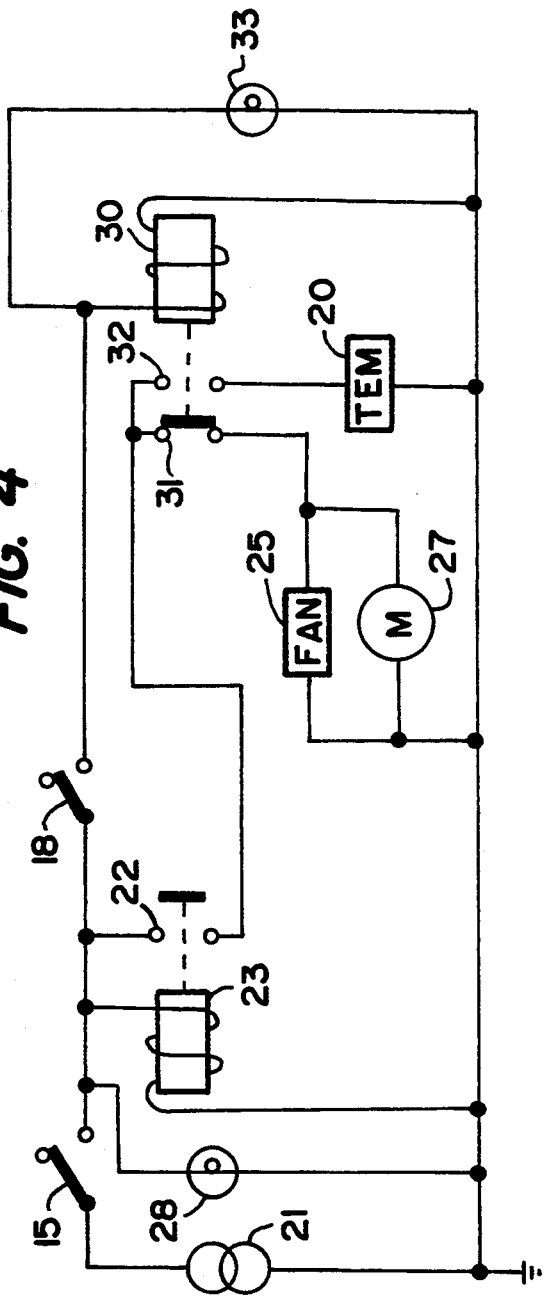
FIG. 4 is an electrical schematic diagram illustrating one of the possible electrical circuits for controlling operation of the embodiment of FIG. 3.

Referring to FIG. 4, an electrical circuit for controlling operation of the embodiment of FIG. 3 includes power switch 15 connected to one side of the electrical power supply 21 for the machine. The other side of power supply 21 is connected to system ground. This power supply is typically 110 volts a.c. convenience power derived from a wall outlet. Connected across the series-connected a.c. supply and switch 15 is the coil of a power relay 23 having a pair of normally open contacts 22. When power switch 15 is closed, relay 23 is energized to close contacts 22 and deliver current to fan 25 in condenser 14 (FIG. 2) and to motor 27 in compressor 12 (FIG. 2). This current is delivered through normally closed contacts 31 of a maintain mode relay 30 described below. Fan 25 and motor 27 are connected in parallel, and this parallel connection is in turn connected in series with normally open contacts 22 of the refrigeration mode relay 23 and the normally closed contacts 31 of the maintain mode relay 30. This refrigeration circuit, including elements 22, 31, 25 and 27, is connected across series-connected power switch 15 and power supply 21.

To effect the maintain mode, the machine is provided with a maintain switch 18 mounted on the top surface of the cabinet 10 (FIG. 1). The maintain switch is connected in series with the coil of maintain mode relay 30 to provide a closed loop series circuit including power supply 21, power switch 15, maintain switch 18 and maintain mode relay coil 30. In addition to normally closed contacts 31, maintain mode relay 30 has a set of normally open contacts 32 connected between the thermoelectrical modules 20 and normally open power relay contacts 22 to receive current therefrom when power switch 15 is closed. This maintain circuit is returned to ground on the other side of modules 20. When both power switch 15 and maintain switch 18 are closed, maintain mode relay 30 is energized to break the refrigeration circuit at contacts 31 and complete the maintain circuit at contacts 32. The thermoelectric modules 20 are thus energized to cool basin 11, but the refrigeration loop is turned off to prevent freezing of the basin by evaporator 11. Although only one thermoelectric module is illustrated in FIG. 4, it will be appreciated that a plurality of such modules may be connected in parallel or series, depending on the particular application.

The circuit of FIG. 4 includes a power on indicator lamp 28 connected between power switch 15 and ground so as to be energized when the power switch 15 is closed. A maintain lamp 33 is connected between maintain switch 18 and ground so as to be energized in the maintain mode (i.e., when both switches 15 and 18 are closed). Lamps 28 and 23 are preferably built into their respective switches 15 and 18 to be illuminated directly on the switch structure.

The circuit of FIG. 4 provides for manual control of the maintain mode. Thus, surgical theater personnel are required to actuate and deactuate the maintain switch 18 in order to keep the temperature of basin 11 at or near the freezing temperature of sterile medium in the basin. Thermoelectric modules 20 are designed and mounted to maintain the temperature close to that freezing temperature, but there are many variables that preclude accuracy in this regard. For example, if the volume of fluid in the basin is relatively small, the temperature maintained in the fluid by the thermoelectric module arrangement will be lower than when a greater fluid volume is provided. To overcome this problem, the maintain mode may be controlled by a timer, or by feeding back a signal corresponding to the sensed temperature of the basin. A time controlled circuit is illustrated in FIG. 5 to which specific reference is now made.

Figure 5:
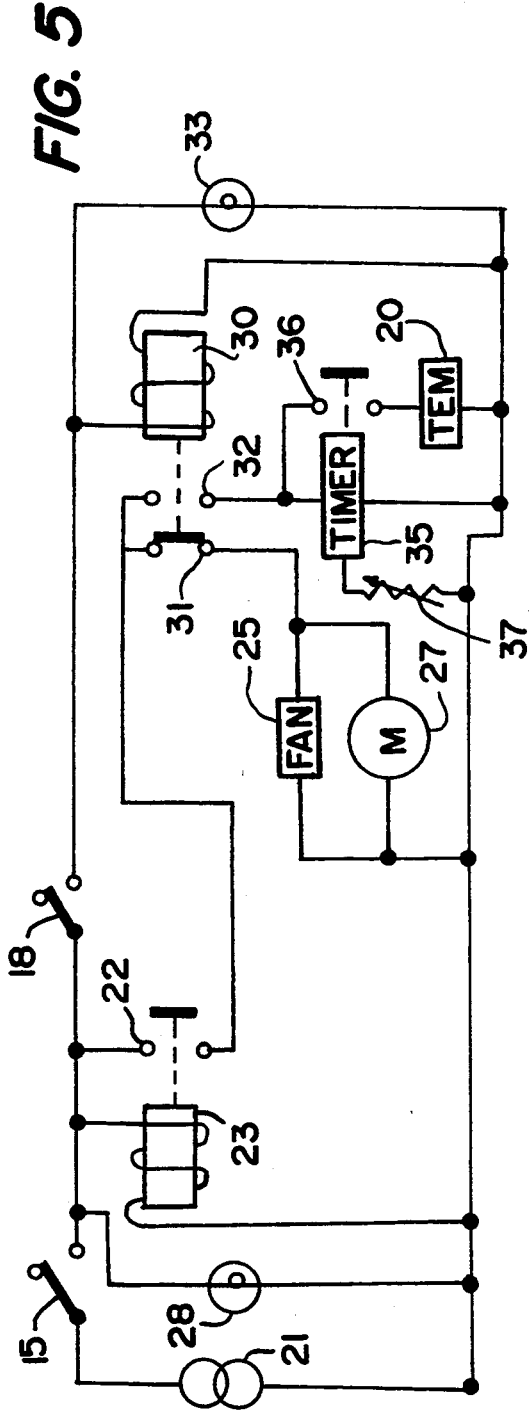
FIG. 5 is an electrical schematic diagram illustrating another possible electrical circuit for controlling operation of the embodiment of FIG. 3.

The circuit of FIG. 5 is identical to the circuit of FIG. 4 except for the portion of the maintain circuit connected between contacts 32 and system ground. Specifically, a timer is connected between contacts 32 and ground. Timer 35 has normally open contacts 36 connected between the maintain contacts 32 and one side of the thermoelectric modules 20. The other side of modules 20 remains connected to ground as in the circuit of FIG. 4. Upon closure of the maintain switch 18 (assuming power switch 15 is also closed), timer 35 is actuated and its contacts 36 are closed to permit current to pass through the thermoelectric modules 20. Timer 35 is the type that continuously cycles between on and off states. During the off portion of the timer cycle, contacts 36 are open and accordingly remove current from the thermoelectric modules 20. The on and off portions of the timer cycle may be equal or not, and these portions may be pre-set or manually adjustable. For manual adjustability, a variable resister 37, or the like, is provided. Variable resistor 37 may be controlled from the top surface of cabinet 10 or may be accessible only from the inside of the cabinet.

Figure 6:
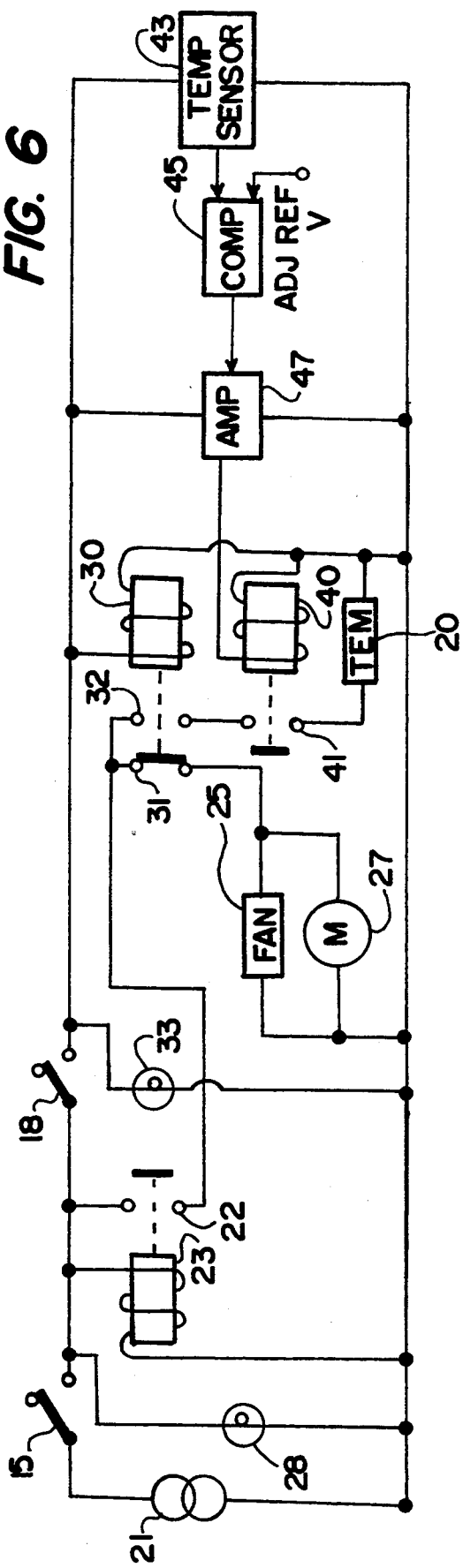
FIG. 6 is an electrical schematic diagram illustrating yet another possible electrical circuit for controlling operation of the embodiment of FIG. 3.

Automatic control of the thermoelectric modules 20 in response to basin temperature may be effected by a circuit such as that illustrated in FIG. 6 to which specific reference is now made. This circuit is the same as the circuit in FIG. 4 except for the maintain circuitry. Specifically, instead of the thermoelectric modules 20 being connected directly to normally open contacts 32 of the maintain relay, normally open contacts 41 of a temperature control relay 40 are interposed between the modules and contacts 32. A temperature sensor 43 is electrically connected between maintain switch 18 and ground, and is mounted on basin 11. Sensor 43 provides a sensor voltage representing the sensed temperature of the basin. A comparator 45 compares the sensor voltage to a reference voltage and provides an output voltage to an amplifier 47 arranged to supply an actuating current to the coil of temperature control relay 40. When the sensor voltage exceeds the reference voltage (or falls below that voltage, if desired), comparator 45 provides a signal to amplifier 47 which, in turn, energizes relay 40 to close contacts 41. Closure of contacts 41 results in current passing through the thermoelectric modules 20 to thereby cool basin 11. The reference voltage of comparator 45 is selected such that the thermoelectric modules are energized as necessary to keep the temperature of the basin at the freezing point of the sterile medium within approximately two percent. The reference voltage at comparator 45 is adjusted manually from inside cabinet 10 to permit the comparator to respond to different temperatures sensed at sensor 43. The operation of the circuit is such that, if the temperature sensed at the basin is below the predetermined temperature (e.g., the freezing temperature of the sterile fluid medium), comparator 45 does not drive amplifier 47 and, therefore, relay 40 and the thermoelectric modules 20 are de-energized. If the sensed temperature rises above the predetermined temperature, the relay and thermoelectric modules are energized to cool the basin. The basin is thus automatically maintained at the predetermined temperature, keeping the sterile medium in the required slush-like phase.

Although thermoelectric modules 20 constitute the preferred means for effecting the maintain mode of the present invention, alternative means may be employed. For example, referring to FIG. 7, two parallel-connected valves may be disposed in the refrigerant flow path at a location between evaporator 13 and compressor 12. Valve 50 is an evaporator pressure regulating valve functioning to regulate the pressure thereacross in the refrigerant fluid. The regulated pressure is adjustable by means of a controller 51. A solenoid controlled valve 52 is normally fully open but can be closed upon actuation of solenoid 53 when the maintain switch 18 is closed. In the refrigeration mode, valve 52 is wide open and the vast majority of the refrigerant fluid flows therethrough without significant restriction. The refrigeration loop thus operates in the manner described above wherein the temperature of basin 11 is lowered to approximately 30° F. When the maintain switch is closed, solenoid 53 is actuated and shuts off valve 52. The refrigerant fluid can thus only flow through the highly restricted flow path comprising valve 50. The evaporator pressure regulator 50, by controlling the pressure of the refrigerant fluid in the closed loop refrigerant path, effectively can control the temperature of that fluid. That is, for constant volume, the fluid pressure is proportional to temperature. Accordingly, the setting of the control 51 on evaporator pressure control valve 50 is chosen to render the temperature of the refrigerant in evaporator 13 at the freezing temperature of the sterile fluid medium in basin 11.

Figure 7:
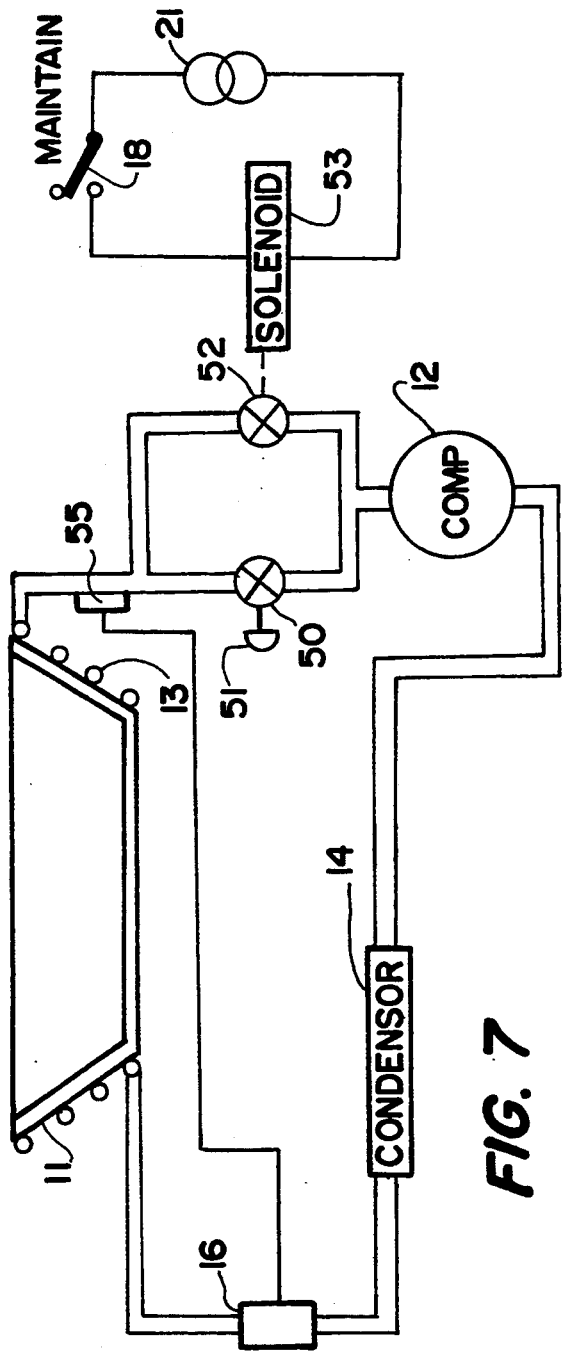
FIG. 7 is a refrigerant flow schematic diagram illustrating another embodiment of the present invention.

It will be appreciated that the embodiment of FIG. 7 permits the refrigeration unit to control the temperature for both the refrigeration mode and the maintain mode. In the refrigeration mode, the evaporator temperature is significantly colder, limited only by expansion control unit 16 operated under the control of a separate temperature sensor sensing the temperature of the refrigerant flowing out of the evaporator 13. Typically, as noted above, this temperature is well below 0° F. In the maintain mode, evaporator pressure regulator valve 50 raises the refrigerant temperature significantly in evaporator 13, thereby keeping the basin temperature at the freezing temperature of the sterile fluid medium.

Figure 8:
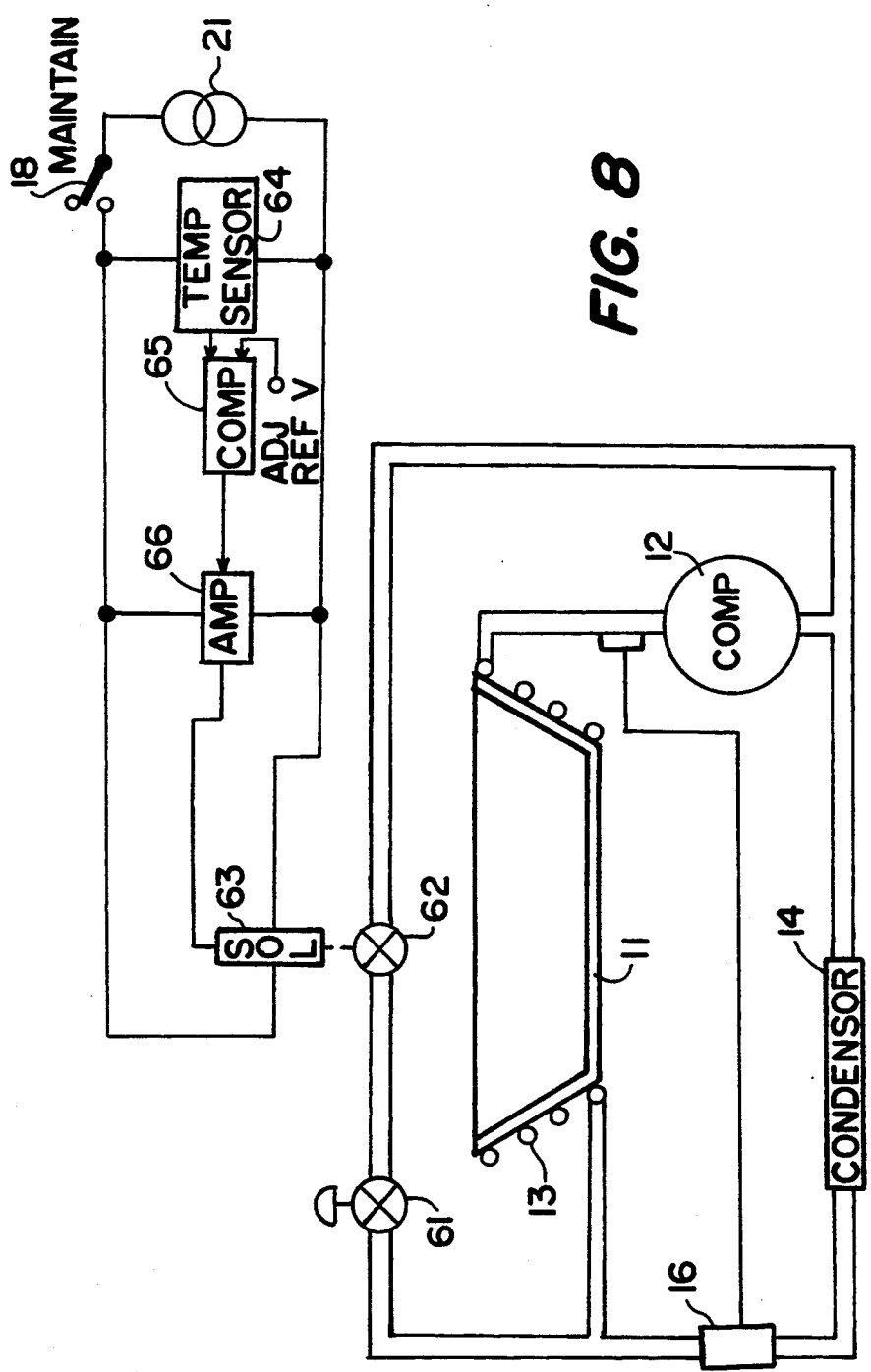
FIG. 8 is a refrigerant flow schematic diagram illustrating still another embodiment of the present invention.

The embodiment of FIG. 8 achieves the maintain mode by means of a hot gas bypass or shunt path for refrigerant fluid. Specifically, the refrigerant flow system includes a shunt path around the evaporator and compressor in the maintain mode. The shunt path includes manually adjustable hot gas pressure regulating valve 61 connected in series with a solenoid controlled valve 62. Valve 62 is opened or closed under the control of a solenoid 63 which may be energized directly in response to closure of maintain switch 18. Alternatively, maintain switch 18 may activate a temperature sensor circuit for controlling the solenoid automatically as a function of the temperature sensed at basin 11; this is the embodiment illustrated in FIG. 8. A temperature sensor 64 is mounted on basin 11 and provides a sensed temperature signal to a comparator 65. The comparator provides a signal to an amplifier 66 whenever the sensed temperature signal achieves a predetermined relationship to a reference voltage also applied to the comparator. Amplifier 66 serves as a driver amplifier for energizing solenoid 63. When maintenance switch 18 is off, valve 62 is closed and no refrigerant fluid flows through the shunt path. The system thus operates in a normal refrigeration mode. When the maintain switch is on or closed, the solenoid 63 is actuated to open valve 62, permitting some refrigerant to bypass the evaporator and condenser. The proportioning of refrigerant flow between the main refrigeration path and the maintain bypass path is determined by the setting of regulating valve 61. The reduced flow of refrigerant fluid through the compressor 12 and evaporator 13 permits the temperature to rise at basin 11 until it reaches the predetermined temperature (e.g., the freezing temperature of the sterile fluid medium) at which comparator 65 causes amplifier 66 to deactuate solenoid 63 and close valve 62. Full refrigerant flow through evaporator 11 and compressor 12 is then restored until the temperature drops below the predetermined temperature, at which time the bypass path is opened once again.

It will be appreciated that the maintain mode feature of the present invention has application in surgical slush machines of the types disclosed in the aforementioned Keyes et al, Templeton and Faries et al patents.

From the foregoing description it will be appreciated that the invention makes available a novel method and apparatus for maintaining surgical slush at a desired temperature.

Having described preferred embodiments of a new and improved method and apparatus for maintaining surgical slush in accordance with the present invention, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. The method of providing a slush phase of a sterile medium in a container for use during a surgical procedure, said method comprising the steps of:
   (a) in a selectively actuable refrigeration mode, cooling said container to a temperature substantially below the freezing temperature of said sterile medium; and
   (b) in a selectively actuable maintain mode, maintaining said container substantially at the freezing temperature of said sterile medium.

2. The method of claim 1 wherein step (b) includes electrically energizing at least one thermoelectric module disposed in thermal energy transfer relation to said container.

3. The method of claim 2 wherein step (a) includes cooling said container by placing an evaporator in thermal energy transfer relation therewith, and flowing a refrigerant fluid through a refrigeration cycle flow path including a compressor, a condenser and said evaporator.

4. The method of claim 3 wherein, during said maintain mode, refrigerant fluid flow through said refrigeration cycle flow path is terminated.

5. The method of claim 4 wherein, during said refrigeration mode, said at least one thermoelectric module is de-energized.

6. The method of claim 3 further including the step of: in said maintain mode, cyclically energizing and de-energizing said at least one thermoelectric module.

7. The method of claim 3 further including the steps of, in said maintain mode:
   (b.1) sensing the temperature at said container; and
   (b.2) energizing and de-energizing said at least one thermoelectric module as a function of the temperature sensed in step (b.1) to maintain said container substantially at said freezing temperature.

8. The method of claim 1 wherein step (a) includes cooling said container by placing an evaporator in thermal energy transfer relation therewith, and flowing a refrigerant fluid through a refrigeration cycle flow path including a compressor, a condenser and said evaporator.

9. The method of claim 8 wherein step (b) includes reducing the rate of refrigerant fluid flow through said evaporator relative to the flow through said evaporator during step (a).

10. The method of claim 9 wherein the step of reducing includes, in said maintain mode, establishing a shunt path for some of said refrigerant fluid to bypass said compressor and evaporator.

11. The method of claim 8 wherein step (b) includes regulating the pressure of refrigerant fluid egressing said evaporator to thereby increase the temperature of the refrigerant fluid in the evaporator relative to the evaporator refrigerant fluid temperature in the refrigeration mode.

12. The method of claim 1 wherein step (a) includes cooling said container to a temperature substantially below 0° F.

13. The method of claim 1 wherein said sterile medium is a normal solution of sodium chloride having a freezing temperature of approximately 30.9° F., and wherein step (a) includes cooling said basin to a temperature of at most −10° F.

* * * * *